(12) United States Patent
Wong et al.

(10) Patent No.: US 7,981,382 B2
(45) Date of Patent: Jul. 19, 2011

(54) DEVICE FOR COLLECTING, TESTING AND STORING FLUIDS

(75) Inventors: Raphael C. Wong, Irvine, CA (US); Ker-Kong Tung, Del Mar, CA (US)

(73) Assignee: Branan Medical Corporation, Irvine, CA (US)

( * ) Notice: Subject to any disclaimer, the term of this patent is extended or adjusted under 35 U.S.C. 154(b) by 944 days.

(21) Appl. No.: 11/153,732

(22) Filed: Jun. 14, 2005

(65) Prior Publication Data

US 2006/0280650 A1 Dec. 14, 2006

(51) Int. Cl.
*G01N 33/00* (2006.01)

(52) U.S. Cl. ........ 422/401; 422/402; 422/408; 422/417; 422/68.1; 422/561

(58) Field of Classification Search .......... 422/50, 422/55, 56, 58, 68.1, 99, 102, 401, 402, 408, 422/417, 561
See application file for complete search history.

(56) References Cited

U.S. PATENT DOCUMENTS

| | | | |
|---|---|---|---|
| 4,873,193 A * | 10/1989 | Jensen et al. | 436/176 |
| 5,119,830 A | 6/1992 | Davis | |
| 5,403,551 A | 4/1995 | Galloway et al. | |
| 5,595,187 A * | 1/1997 | Davis | 600/584 |
| 6,074,606 A * | 6/2000 | Sayles | 422/58 |
| 6,342,183 B1 | 1/2002 | Lappe et al. | |
| 6,680,027 B2 | 1/2004 | Kang et al. | |
| 6,726,879 B2 * | 4/2004 | Ng et al. | 422/58 |
| 6,915,919 B2 * | 7/2005 | Casterlin | 215/247 |
| 2003/0021726 A1 * | 1/2003 | Wu et al. | 422/58 |
| 2003/0021727 A1 | 1/2003 | Weyker et al. | |
| 2003/0021736 A1 | 1/2003 | Kang et al. | |
| 2004/0081581 A1 | 4/2004 | Mount et al. | |

FOREIGN PATENT DOCUMENTS

WO 2005050169 A 6/2005

OTHER PUBLICATIONS

International Search Report and Written Opinion of the International Searching Authority.
European Patent Office Search Report dated Jan. 28, 2011 for European Patent Application No. 06771234.9.

* cited by examiner

*Primary Examiner* — Sam P Siefke
(74) *Attorney, Agent, or Firm* — Vic Lin; Innovation Capital Law Group, LLP

(57) ABSTRACT

A device for collecting, testing and storing fluids includes a container and a removable cap. Body fluids, such as urine, are collected in the container. The cap defines a test strip holder that receives one or more drug test strips and an adulteration strip. An opening defined through a bottom of the cap provides fluid communication between the container and the cap. When tilted, fluid from the container enters the cap through the hole. A variety of plugs may be employed to block the opening and thereby prevent fluid communication between the container and the cap after fluid has entered the cap. The remaining uncontaminated and untested body fluid is stored in the container and thus made available for further confirmation testing. Associated methods for collecting, testing and storing fluids with a single device are also provided. A method of manufacturing the foregoing test device is also provided.

11 Claims, 7 Drawing Sheets

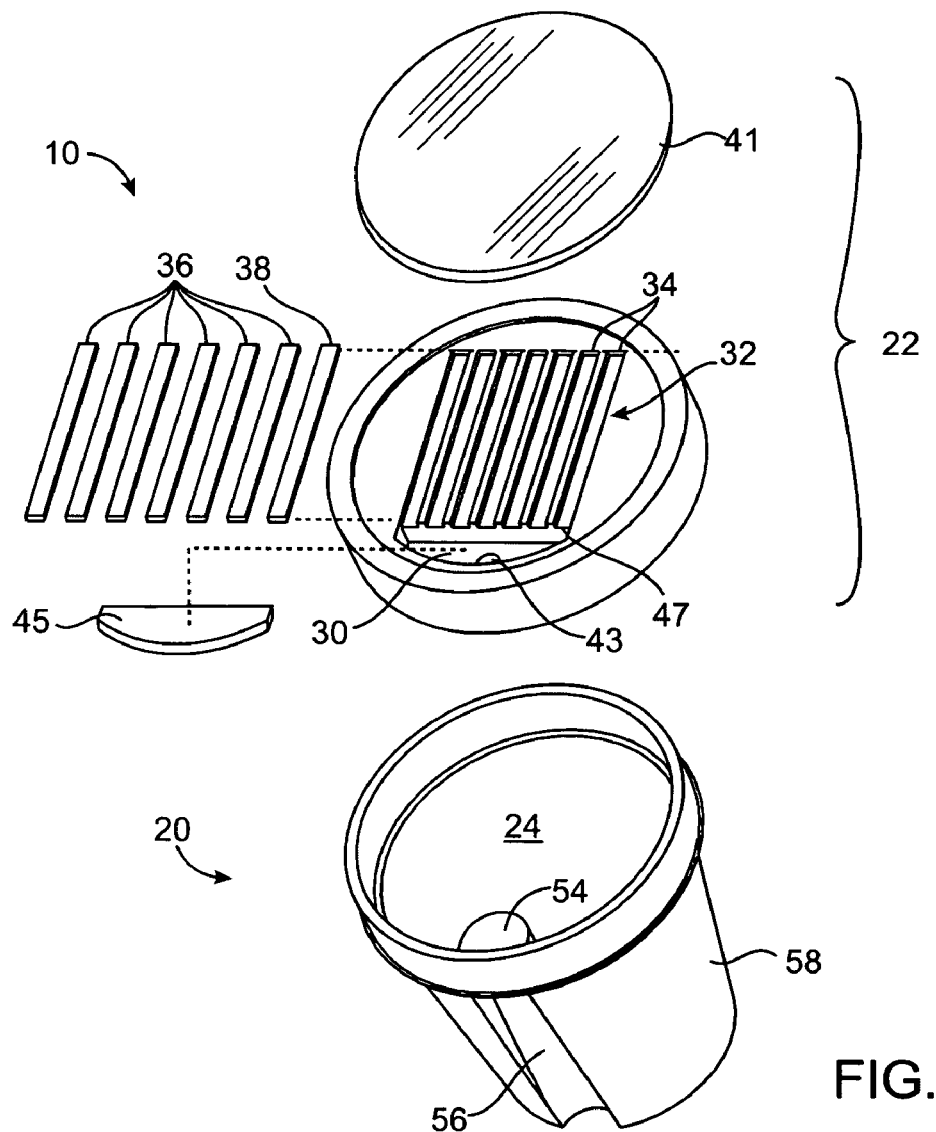
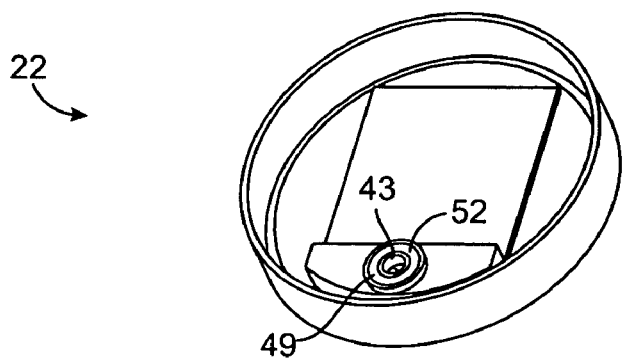

DEVICE FOR COLLECTING, TESTING AND STORING FLUIDS

BACKGROUND OF THE INVENTION

1. Field of the Invention

The present invention relates generally to devices for testing liquid samples for analytes.

2. Description of Prior Art and Related Information

The need for testing for drugs of abuse continues to grow in employment, schools, rehabilitation centers and various other fields. Since the primary body fluid tested is urine, testers naturally wish to minimize opportunities for direct contact. Along with this growing need for testing is a concurrent need to confirm the test results generated. Accordingly, it is preferable to maintain uncontaminated samples of the tested fluids which may be sent, for example, to a licensed laboratory in the event confirmation is required. Since most tests are performed by laypersons, it is also preferable to accomplish the foregoing with simplicity while minimizing the potential for operator error and contact with the urine.

Of course, collecting the urine, testing it for drugs of abuse and reserving an uncontaminated sample can be accomplished in several steps using several different devices. Such an approach obviously increases the exposure of the user to the urine and, thus, the opportunities for undesired contact.

Attempts to address all of the foregoing needs in a single apparatus have led to complicated devices which are expensive to manufacture and complex to operate. The complexity in these devices make it difficult for the user to determine whether sufficient fluid has been brought into contact with the test strips. Still other devices include a cup with a drug test cassette disposed therein. While such devices enable urine to be collected and tested in a single apparatus, they do not effectively separate the assays and tested urine from the untested urine. Since chemicals from the assays can easily leech into the remaining fluid, these devices fail to reserve an uncontaminated portion of the urine for confirmation. Also, many cup devices currently available in the market feature opaque layers through which the test results are displayed, thereby rendering it difficult for users to view the results.

SUMMARY OF THE INVENTION

The present invention provides structures and methods which overcome the deficiencies in the prior art.

In one aspect, a drug test device is provided for collecting, testing and reserving a sample fluid. The device is particularly configured to test body fluids, such as urine, for the presence of drugs of abuse. The device comprises a container defining a reservoir and a cap configured removably coupled to the container. The cap houses at least one test strip and defines an opening to enable fluid communication between the test strip and the reservoir of the container. The device also includes a plug configured to entirely block the opening so as to close fluid communication between the test strip and the reservoir. The plug may comprise a stop formed as an integral portion of the container.

The cap is movable with respect to the container between a first configuration where the opening is unblocked by the stop and a second configuration wherein the opening is blocked by the stop. In a preferred embodiment, the cap is rotatable with respect to the container. The cap may also comprise a transparent top. The test strip comprises a colored reagent. An adulteration test strip may also be housed in the cap. The plug may coupled to, or separate from, the cap.

The device may also comprise a second cap removably disposed on top of the first cap. In such an embodiment, the plug may be formed as part of the second cap such that the second cap comprises the plug. The device may further comprise a tamperproof tape disposed on top of the second cap.

In another aspect, a drug testing device is provided comprising a container, a cap configured to be removably coupled to the container, and a movable plug. The container defines a reservoir. The cap houses at least one test strip and defines an opening to enable fluid communication between the test strip and the reservoir. The plug is movable between a first configuration, so as to prevent the fluid communication between the test strip and the reservoir, and a second configuration, so as to enable the fluid communication between the test strip and the reservoir. In the first configuration, the plug entirely blocks the opening. In the second configuration, the opening is at least partially open to the reservoir.

The plug may comprise a stop formed as an integral portion of the container. The cap may be rotatable with respect to the container. The cap may also comprise a transparent top. The test strip comprises a colored reagent. The device may further comprise an adulteration test strip housed in the cap. The plug may be coupled to, or separate from, the cap.

The device may further comprise a tamperproof mechanism, including a second cap removably disposed on top of the first cap. The plug may be included in the second cap. The device may also comprise a tamperproof tape disposed on top of the second cap.

In a further aspect, a method of testing a bodily fluid for drugs is provided. The method comprises the steps of collecting a sample of body fluid with a container, moving a first portion of the sample into a cap having at least one test strip, testing the first portion for a presence of a drug, and separating the first portion from a second portion of the sample remaining in the container.

The step of moving the first portion of the sample into the cap having the at least one test strip comprises tilting the container until a color change, preferably red, appears in the window area. Once the color change is observed, the container may simply be tilted back to an upright position. The step of separating the first portion from the second portion of the sample remaining in the container comprises blocking an opening defined in the cap. The step of blocking the opening defined in the cap comprises rotating the cap with respect to the container. The step of blocking the opening defined in the cap also comprises blocking the opening with a plug.

The method may further comprise testing the second portion of the sample for confirmation. In the preferred method, a tamperproof mechanism may be coupled to the cap. The step of coupling the tamperproof mechanism to the cap comprises disposing a second cap on top of the first cap. Coupling the tamperproof mechanism to the cap further comprises disposing a tamperproof tape on top of the second cap.

A method of manufacturing a liquid sample test device is also provided. The method comprises providing a container, providing a cap to be removably coupled to the container, disposing at least one test trip on top of a planar surface of the cap, providing fluid communication between the at least one test strip and the container, providing a plug for closing fluid communication between the at least one test strip and the container, and disposing a clear top layer on top of the test strip.

The step of providing the cap to be removably coupled to the container comprises configuring the cap to be rotatable with respect to the container. The step of providing the plug for closing fluid communication between the at least one test strip and the container comprises forming the plug as an integral portion of the container.

In summary, a device for collecting, testing and storing fluids includes a container and a removable cap. Body fluids, such as urine, are collected in the container. The cap defines a test strip holder that receives one or more drug test strips and an adulteration strip. An opening defined through a bottom of the cap provides fluid communication between the container and the cap. When tilted, fluid from the container enters the cap through the hole. A variety of plugs may be employed to block the opening and thereby prevent fluid communication between the container and the cap after fluid has entered the cap. The remaining uncontaminated and untested body fluid is stored in the container and thus made available for further confirmation testing. Associated methods for collecting, testing and storing fluids with a single device are also provided. A method of manufacturing the foregoing test device is also provided.

The invention, now having been briefly summarized, may be better appreciated by the following detailed description.

BRIEF DESCRIPTION OF THE DRAWINGS

FIG. 1 is an exploded, perspective view of a preferred embodiment of a drug test device to the invention;

FIG. 2 is a bottom perspective view of a preferred cap;

DETAILED DESCRIPTION OF THE PREFERRED EMBODIMENTS

Figure 4:
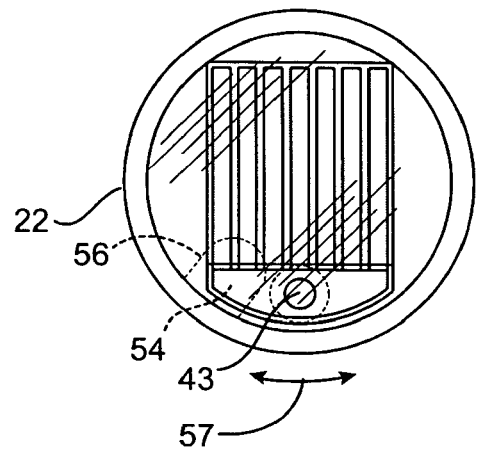
FIG. 4 is a top view of the preferred embodiment of the drug test device in an open configuration.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

A preferred embodiment of a drug test device is illustrated in an exploded, perspective view in FIG. 1 and designated generally by the reference numeral 10. The device 10 includes a container 20 and a cap 22 that is configured to be removably coupled thereto. The container 20 defines a reservoir 24 for collecting and storing a sample of fluid, such as urine. While the container 20 is generally shaped as a cup in the preferred embodiment, the container 20 comprises several unique features as described further below.

In FIG. 1, the preferred cap 22 includes a chamber 30 that is in fluid communication with a test strip holder 32. The test strip holder 32 includes at least one elongate recess 34 configured to receive a drug test strip 36, such as an assay strip. In the preferred embodiment, the test strip holder 32 comprises a plurality of recesses 34 configured to receive a plurality of drug test strips 36. At least one of the recesses 34 may be configured to receive an adulteration test pad 38 so that the device 10 may be used for both drug testing as well as confirmation of the lack of adulteration. The recesses 34 lie side by side along a plane that is substantially parallel to a top planar layer 41 of the cap 22. The top planar layer 41 is preferably transparent. Therefore, when the cap 22 is assembled to the container 20 and the device 10 sits in an upright position on top of a table, for example, the results of the strips 36, 38 are displayed through the transparent top 41 such that they may be easily viewed from the top of the device 10.

In FIGS. 1 and 2, an opening, or hole, 43 is formed in the chamber 30 of the cap 22 so as to provide fluid communication between the reservoir 24 of the container 20 and the strips 36, 38 in the holder 32. The chamber 30 is preferably sized to receive an absorbent pad 45 which serves to direct fluid from the container 20 to the various strips 36, 38. The juxtaposed recesses 34 are positioned such that each upstream end 47 opens into the chamber 30. Alternatively stated, the chamber 30 is positioned adjacent to the upstream end 47 of each recess 34 such that fluid wicking through the absorbent pad 45 may be directed to each test strip 36, 38 held within the recesses 34. In FIG. 2, the hole 43 is further defined by a protrusion 49, shown in the preferred embodiment as a disk, which provides a surface, or seat 52, in order to facilitate a sealing relationship as described further below.

In FIG. 1, a plug, or stop, 54 is provided to prevent fluid in the container 20 from entering the chamber 30 of the cap 22. It will be appreciated that the plug 54 maintains the integrity of the untested fluid remaining in the container 20 by preventing any of the chemicals from the test strips and the tested fluid portions from being mixed back in with the untested fluid. In the preferred embodiment, the plug 54 is formed as an integral portion of the container 20. In particular, container 20 comprises an indentation 56 formed axially, or vertically, along a sidewall 58.

Figure 3:
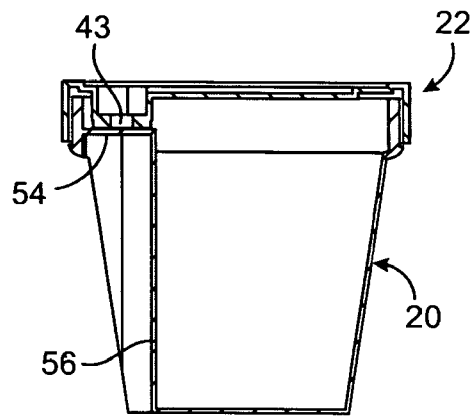
FIG. 3 is a cross-sectional view of the preferred embodiment of the drug test device as assembled.
Figure 5:
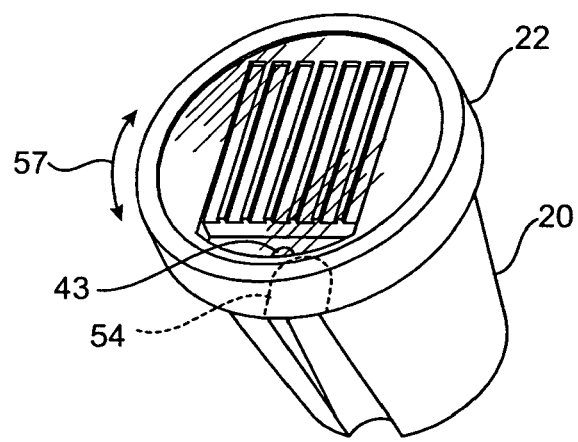
FIG. 5 is a perspective view of the preferred embodiment of the drug test device in a closed configuration.
Figure 6:
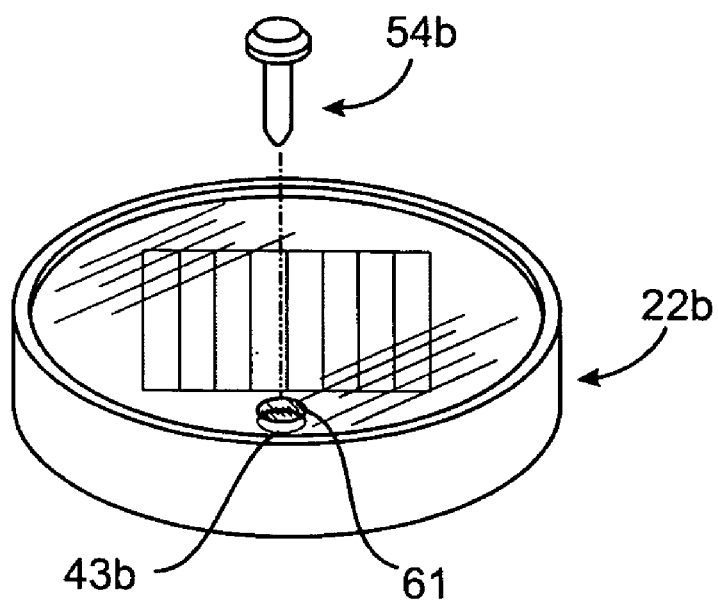
FIG. 6 is a perspective view of a second preferred embodiment of a cap.
Figure 7:
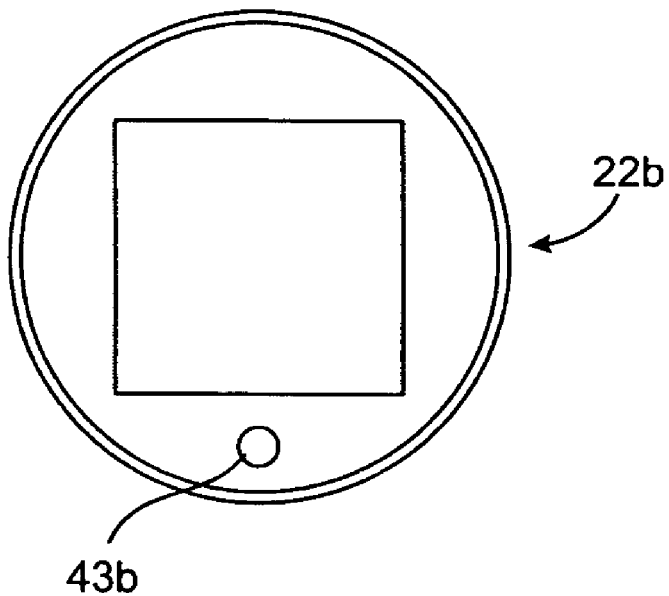
FIG. 7 is a bottom view of the second preferred embodiment of the cap.

FIGS. 3-5 illustrate the device 10 as assembled with the cap 22 coupled to the container 20. For purposes of clarity, the test strips 36, adulteration strip 38 and absorption pad 45 have been omitted in order to illustrate the opening and closing of the opening 43. In the illustrated embodiment, the plug 54 comprises an inner horizontal surface formed at the top of the indentation 56 which is configured to form a seal with the annular protrusion 49 of the cap 22 so as to entirely block, or close, the opening 43.

When the plug 54 is formed as a fixed, integral portion of the container 20 as shown in the first preferred embodiment in FIGS. 1-5, the opening 43 and the plug 54 are configured to be movable with respect to each other in order provide an open configuration, where there is fluid communication between the cap 22 and the container 20, and a closed configuration, where no fluid may travel between the cap 22 and the container 20. In the preferred embodiment, the cap 22 is not only removably coupled to the container 20, but also movable with respect to the container 20 when assembled thereon. As indicated by the bidirectional arrow 57 in FIGS. 4 and 5, the cap 22 is rotatable with respect to the container 20 in order to facilitate the open and closed configurations. An open configuration is illustrated in FIG. 4 where fluid from the container 20 may enter the cap 22 through the opening 43. In the closed configuration illustrated in FIG. 5, the cap 22 is moved, or more specifically rotated, with respect to the container 20 so that the opening 43 is entirely blocked by the plug 54. To facilitate the sealing of the aperture, indicia, such as a dot, may be printed on the top surface of the cap 22 to indicate the position of the aperture on the opposite side. This aids the user in opening and closing the cap.

In operation, a liquid sample is collected in the reservoir 24 of the container 20 as shown in FIGS. 1-5. The cap 22 is coupled to the container 20. The cap 22 is then moved, preferably rotated, with respect to the container 20 to enable fluid communication between the cap 22 and the container 20. The entire device 10 is tilted to a testing position, wherein a portion of the liquid sample from the container 20 will seep through the opening 43 and saturate absorbent pad 45. After saturation, the liquid sample on the pad 45 will be delivered to sample pads on the test strips 36, 38 via capillary action and be migrated to a color reagent portion, such as a gold conjugate pad, on each test strip 36. The liquid sample will then dissolve the gold conjugate, thereby causing a color change, such as a red colored solution, to appear. The colored solution then migrates via capillary action along the strips 36 in an upward or downstream direction, i.e., a direction away from the absorbent pad 45. As soon as the red colored gold conjugate solution shows up in a visible area, such as a window, of the cap 22, the user can then restore the device 10 back to the upright position. The cap 22 is then moved, or rotated, with respect to the container to plug the opening 43 and thus close off fluid communication between the cap 22 and the container 20. The user then simply waits for the completion of the test.

A preferred method of manufacturing is also provided. In FIG. 1, the top layer 41 is assembled on top of the strips 36, 38 after placing the strips 36,38 in the recesses 34. Unlike other test devices where test strips have to be embedded in a complex wall structure of the device, the strips 36, 38 here are simply laid into the recesses 34 and the absorption pad 45 placed into the chamber 30. Afterwards, the clear display layer 41 is simply fitted, or otherwise assembled, on top of the strips 36,38 and absorption to become a part of the cap 22.

In further embodiments of the cap illustrated in FIGS. 6-9, elements of similar structure are designated by the same reference numerals followed by the lower case letters "b" and "c."

It will be appreciated that a variety of plugs may be employed to close the opening 43 in the cap 22 and prevent fluid communication between the container 20 and cap 22. For example, in FIGS. 6 and 7, a separate plug 54b may be removably coupled to a cap 22b. The cap 22b includes an opening 43b to receive fluid from the container (not shown). The top of the opening 43b is temporarily sealed by a thin sheet of material 61 which may be easily punctured, removed or broken through. As examples and not by way of limitation, the top seal 61 may comprise plastic, paper or any other material sturdy enough to prevent liquid from seeping therethrough, yet soft enough to be punctured or broken through by manual force. In operation, when sufficient fluid has entered the cap 22b and the opening 43b needs to be sealed from the rest of the container, the user simply punctures the top seal 61 with the plug 54b and inserts the plug 54b all the way through, or at least to a depth sufficient to seal the cap 22b from the fluid remaining in the container.

Figure 8:
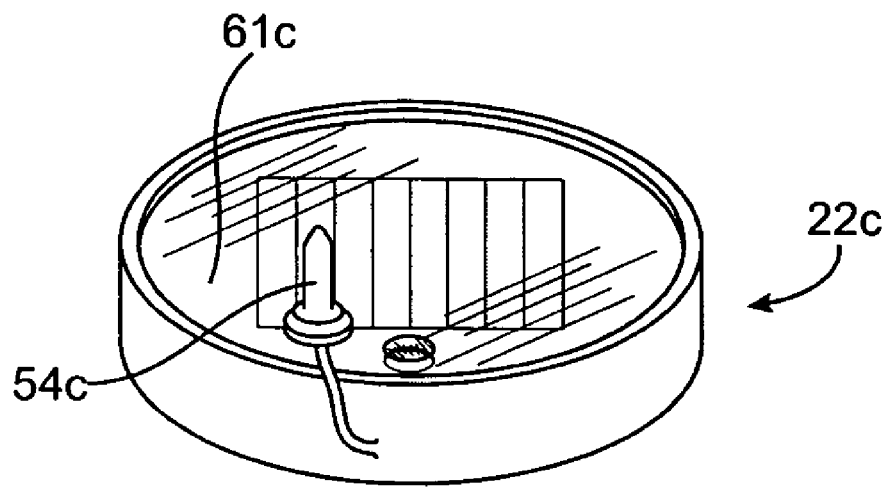
FIG. 8 is a top view of a third preferred embodiment of a cap.

In a further embodiment of a cap 22c illustrated in FIG. 8, a plug 54c is coupled to the cap 22c. Similar to the second preferred embodiment of a cap 22b illustrated in FIGS. 6 and 7, the cap 22c in FIG. 8 also includes a temporary top seal 61c which may be punctured, removed or broken through. In operation, the plug 54c is inserted through the top of aperture 43c.

Figure 9:
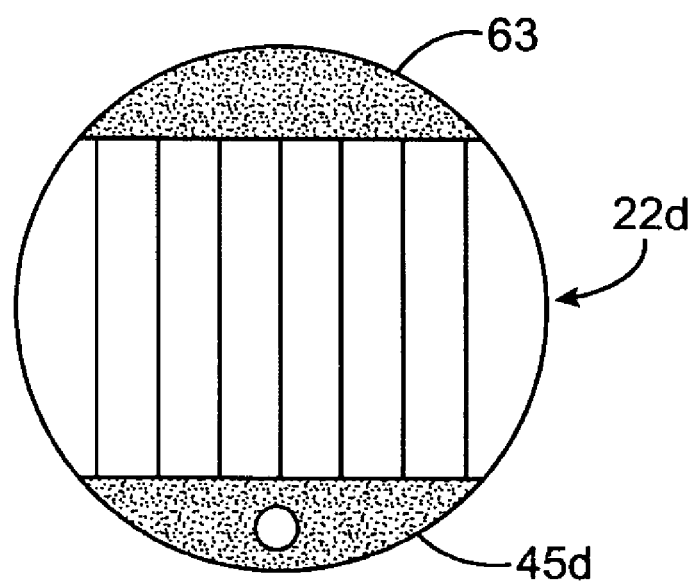
FIG. 9 is a top view of the third preferred embodiment of the cap.

A further preferred embodiment of a cap 22d is illustrated in FIG. 9. The cap 22d comprises a first upstream absorption pad 45d and a second downstream absorption pad 63 located an opposite end thereof. The first upstream absorption pad 45d functions in a similar manner as the absorption pad 45 of the first preferred embodiment discussed above. Accordingly, the first upstream absorption pad 45d is in fluid communication with an opening in the cap 22d through which fluid from the container enters into the cap 22c. The first upstream absorption pad 45d absorbs the fluid from the opening and directs the fluid to the test strip holder 32d. The second downstream absorption pad 63, located at an opposite end of the first pad 45d, absorbs any excess fluid from the test strips 36d.

Figure 10:
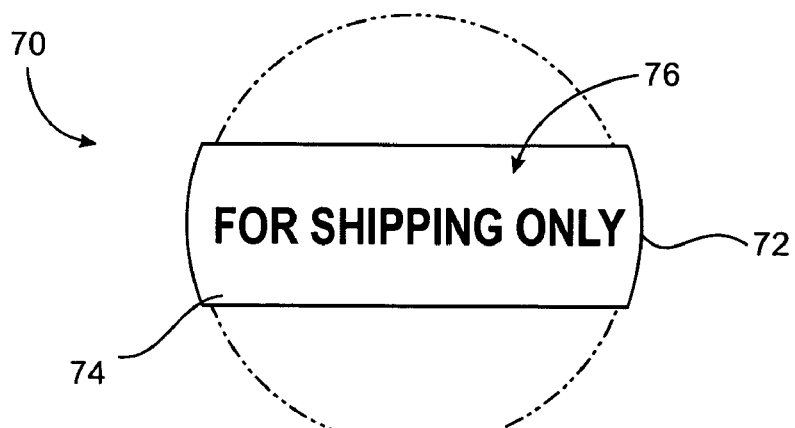
FIG. 10 is a top view of a first preferred tamperproof mechanism.
Figure 11:
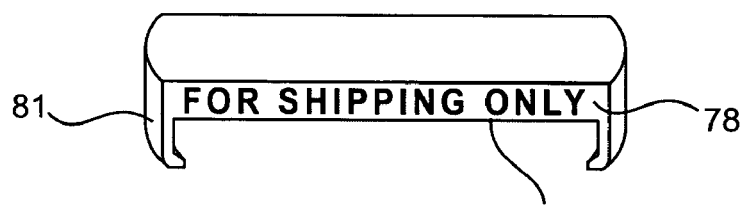
FIG. 11 is a side view of the first preferred tamperproof mechanism.
Figure 12:
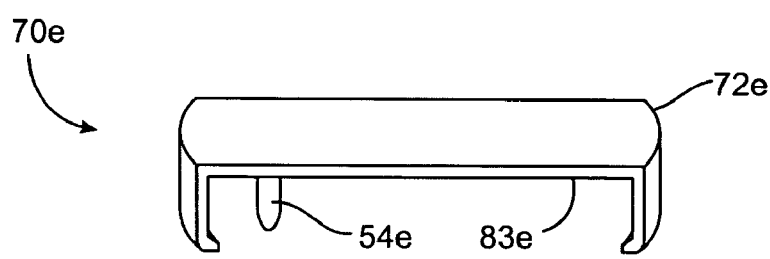
FIG. 12 is a side view of a second preferred tamperproof mechanism.

The device 10 may also include a tamperproof mechanism, such as a second cap or overcap, with or without tape. In FIGS. 10-11, a tamperproof mechanism 70 comprises a second cap 72 configured to be disposed on top of the first, original cap 22-22d discussed above in connection with FIGS. 1-9. In FIGS. 10-12, the second cap, or overcap, 72 includes a top surface 74 upon which indicia 76, such as "For Shipping Only," may be printed. Indicia 76 may also be printed on sidewalls 78 of the cap second cap 72. The second cap 72 includes end tabs, or clips, 81 projecting downwardly from a bottom surface 83. The clips 81 are configured to removably couple the second cap 72 to the first cap 22-22d previously described.

In further embodiments of the tamperproof mechanism illustrated in FIGS. 12-16, elements of similar structure are designated by the same reference numerals followed by the lower case letters "e" and "f."

Figure 13:
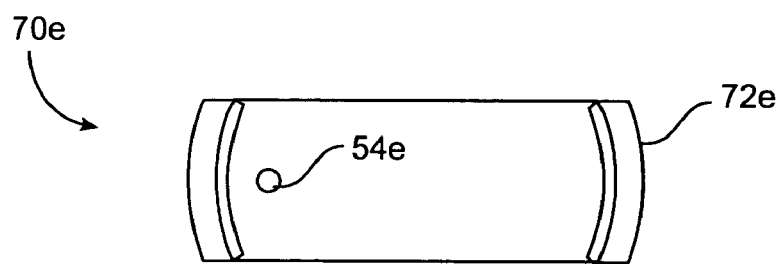
FIG. 13 is a bottom view of the second preferred tamperproof mechanism.

In FIGS. 12 and 13, a plug for the aperture in the cap may be included as part of an alternate tamperproof mechanism 70e. The mechanism 70e includes a second cap 72e having a plug 54e projecting downwardly from a bottom surface 83e. When used in connection with the cap 22b illustrated in FIGS. 6 and 7, for example, the plug 54e is configured to block the opening 43b in order to seal the cap 22b from the container.

Figure 14:
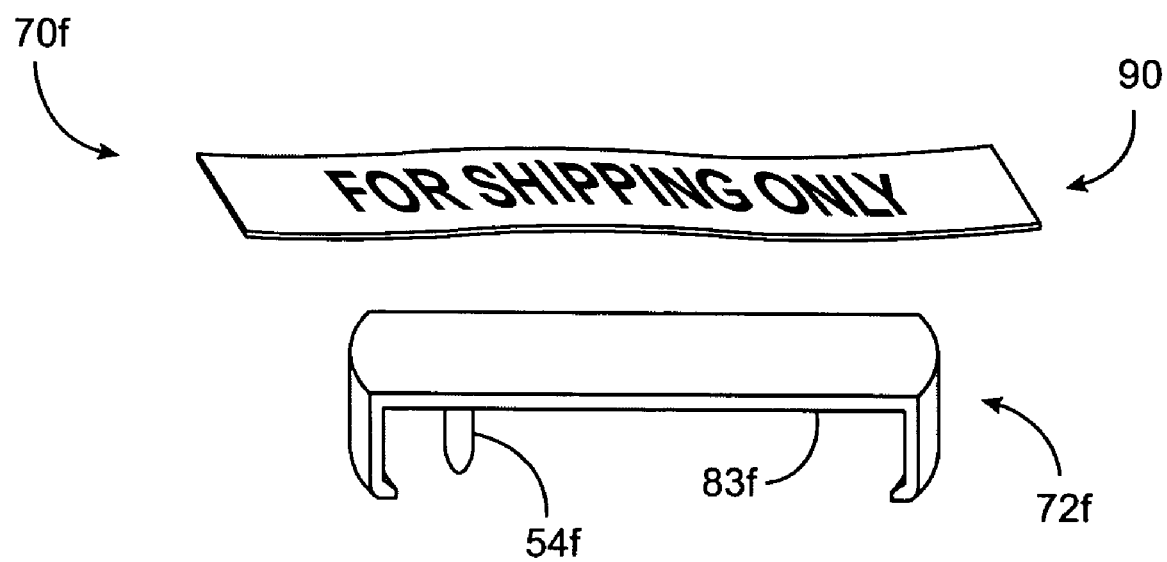
FIG. 14 is an exploded, perspective view of a third preferred tamperproof mechanism.

In FIG. 14, an alternate embodiment of a tamperproof mechanism 70f includes a second cap 72f and tamperproof tape 90. The second cap 72f also includes a plug 54f projecting downwardly from a bottom surface 83f. Tabs may be omitted from the second cap 72f since the tape 90 serves to secure the second cap 72f to a first, original cap.

Figure 15:
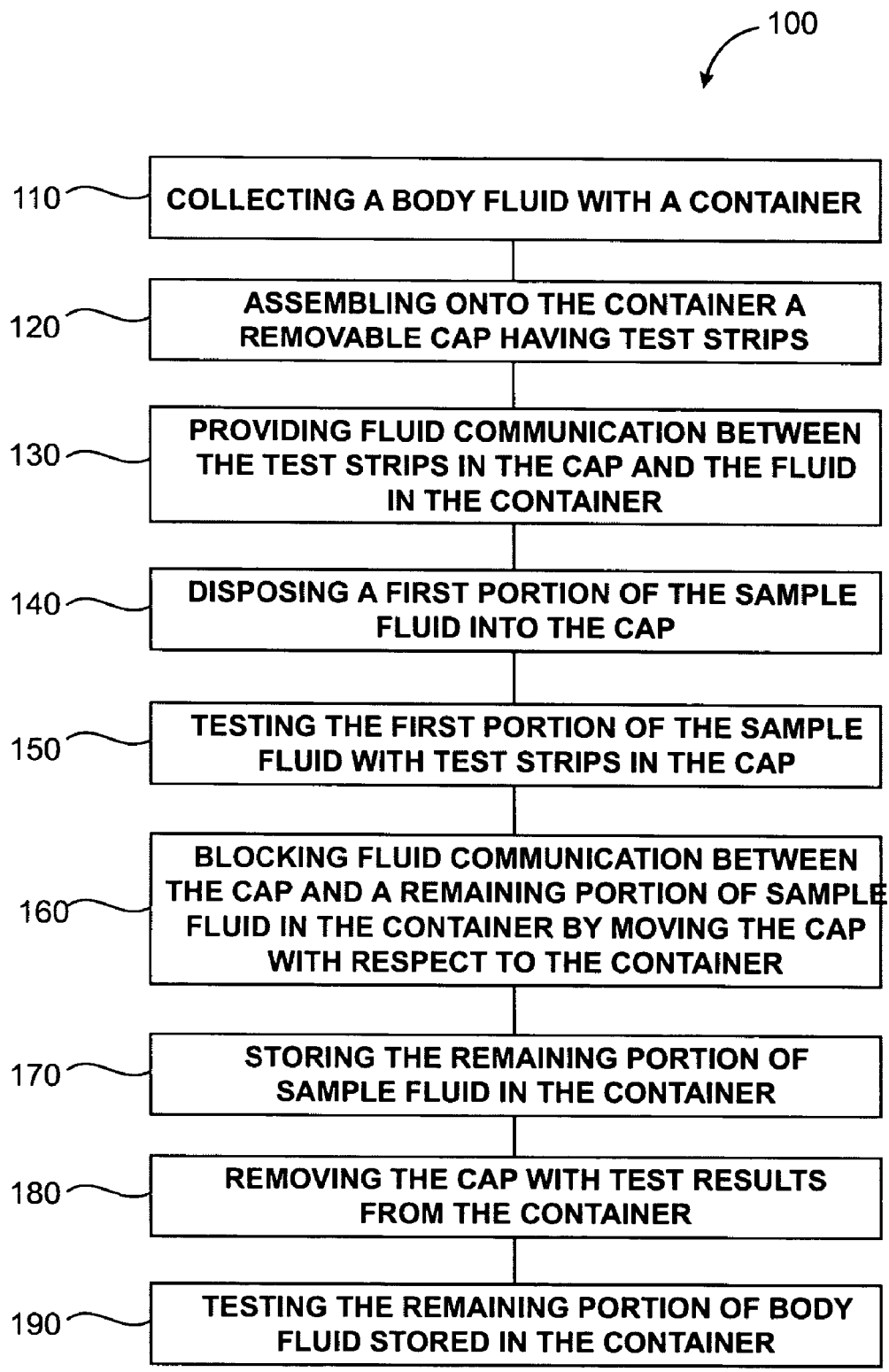
FIG. 15 is a diagram of a preferred method for collecting, testing and storing a body fluid for drugs of abuse.

A preferred method for collecting, testing and storing a body fluid for drugs of abuse is also provided. FIG. 15 illustrates a preferred method 100 according to the invention. The method comprises a step 110 of collecting a body fluid with a container. Step 120 includes assembling onto the container a removable cap having test strips, such as immunoassays, which test for the presence of drugs of abuse. As discussed above, the removable cap may also include an adulteration strip in order to test the integrity of the body fluid. In step 130, fluid communication is provided between the test strips in the cap and the fluid in container. As discussed above, this may be accomplished by providing an aperture in the cap and moving the cap such that the aperture is unblocked, or open to the container. Step 140 includes disposing a first portion of the sample fluid into the cap. In a preferred method, this may be accomplished by simply tilting the entire device such that the first portion of the fluid in the container is directed into the cap. The first portion of the fluid engages a reagent portion and dissolves the conjugates at an upstream end of each test strip, thereby causing a color change, such as a red colored solution, to appear. Once the color change in the strips 36 is detected through the clear display 41 or through a window area, the device may be tilted back and restored to its initial upright position. In step 150, the first portion fluid disposed in the cap is tested for the presence of drugs of abuse. Adulteration testing may also be included in this step.

In step 160, fluid communication between the cap and a remaining portion of the sample fluid in the container is blocked, or closed, in order to maintain the integrity of the remaining portion of sample fluid. This may be important particularly when the remaining portion of sample fluid needs to be tested for confirmation of the earlier test results. As discussed above, closing fluid communication between the cap and the container may be accomplished by a variety of ways. In one aspect, the cap may be moved, or rotated, with respect to the container in order to block an opening in the cap with a plug formed integrally with the container. In another aspect, the opening in the cap may be blocked by a separate plug inserted through the opening. Alternatively, a tamperproof mechanism, such as a second cap, may be formed with an integral plug which would then be inserted through the aperture when the second cap is coupled on top of the first, original cap.

Step 170 includes storing the remaining portion of sample fluid in the container. It will be appreciated that this step also includes maintaining the integrity of the remaining portion of sample fluid because chemicals from the test strips in the cap are sealed off from contact with the remaining portion in the container.

In some instances, the test results provided by the cap may need to be confirmed. Accordingly, in step 180, the cap is removed from the container, thereby providing access to the uncontaminated remaining portion of sample fluid in the container. Step 190 includes testing the remaining portion of sample fluid stored in the container to, for example, confirm the integrity of the earlier results.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A method of testing a bodily fluid for drugs, comprising:
   collecting a sample of fluid with a container comprising a vertical indentation along an outer sidewall of the container, from the bottom of the container leading up to a top horizontal wall that forms a stop;
   placing a cap including a solid clear cover onto the container, wherein the cap has an opening formed in a chamber of the cap, and the chamber is further configured to receive an absorbent pad to enable fluid communication between the cap and the container, wherein the opening is offset from the center axis of the cap;
   tilting the container such that the vertical indentation rests on a surface in order to prevent rotation of the container along the surface;
   moving a first portion of the sample into the cap having at least one test strip;
   testing the first portion for a presence of a drug;
   viewing a test result through the clear cover; and
   sealing the first portion from a second portion of the sample remaining in the container by rotating the cap with respect to the container to align the opening with the stop.

2. The method of claim 1, further comprising testing the second portion of the sample for confirmation.

3. The method of claim 2, further comprising coupling a tamperproof mechanism to the cap.

4. The method of claim 3, wherein the cap comprises a first cap; and coupling the tamperproof mechanism to the cap comprises disposing a second cap on top of the first cap.

5. The method of claim 4, wherein coupling the tamperproof mechanism to the cap further comprises disposing a tamperproof tape on top of the second cap.

6. A method of testing a bodily fluid for drugs, comprising:
   collecting a sample of fluid with a container comprising a vertical indentation along an outer sidewall of the container, from the bottom of the container leading to a top horizontal wall that forms a stop;
   placing a cap including a solid clear cover onto the container, wherein the cap further comprises a cap chamber in fluid communication with at least one recess, wherein the cap chamber has an opening to enable fluid communication between the cap chamber and the container, wherein the opening is offset from the center axis of the cap;
   moving a first portion of the sample into the cap chamber in fluid communication with the at least one recess;
   testing the first portion for a presence of a drug;
   viewing a test result through the clear cover; and
   sealing the first portion from a second portion of the sample remaining in the container by rotating the cap with respect to the container to align the opening to the stop.

7. The method of claim 6, wherein moving the first portion of the sample into the cap having the at least one test strip comprises tilting the container towards one side of the container.

8. The method of claim 7, further comprising testing the second portion of the sample for confirmation.

9. The method of claim 8, further comprising coupling a tamperproof mechanism to the cap.

10. The method of claim 9, wherein coupling a tamperproof mechanism to the cap further comprising disposing a second cap on top of the cap.

11. The method of claim 10, wherein coupling the tamperproof mechanism to the cap further comprises disposing a tamperproof tape on top of the second cap.

* * * * *